(12) United States Patent
Albrecht et al.

(10) Patent No.: US 8,696,996 B2
(45) Date of Patent: Apr. 15, 2014

(54) DEVICE AND METHOD FOR GENERATING A BARRIER DISCHARGE IN A GAS FLOW

(71) Applicant: Reinhausen Plasma GmbH, Regensburg (DE)

(72) Inventors: Andreas Albrecht, Regensburg (DE); Eckart Theophile, Wenzenbach (DE)

(73) Assignee: Reinhausen Plasma GmbH, Regensburg (DE)

( * ) Notice: Subject to any disclaimer, the term of this patent is extended or adjusted under 35 U.S.C. 154(b) by 0 days.

(21) Appl. No.: 13/782,246

(22) Filed: Mar. 1, 2013

(65) Prior Publication Data

US 2013/0177473 A1 Jul. 11, 2013

Related U.S. Application Data

(63) Continuation of application No. PCT/EP2011/063358, filed on Aug. 3, 2011.

(30) Foreign Application Priority Data

Sep. 2, 2010 (DE) .......................... 10 2010 044 252

(51) Int. Cl.
*B01J 19/08* (2006.01)

(52) U.S. Cl.
USPC .................................................. 422/186.04

(58) Field of Classification Search
USPC .................................................. 422/186.04
See application file for complete search history.

(56) References Cited

U.S. PATENT DOCUMENTS

| 4,737,885 A | 4/1988 | Akutsu |
| 6,119,455 A | 9/2000 | Hammer et al. |
| 6,461,409 B1 | 10/2002 | Neff et al. |
| 2003/0180199 A1 | 9/2003 | Kim et al. |
| 2006/0189168 A1 | 8/2006 | Sato et al. |
| 2008/0056934 A1 | 3/2008 | Tsui |

FOREIGN PATENT DOCUMENTS

| DE | 19525754 A1 | 1/1997 |
| DE | 19635232 A1 | 3/1998 |
| DE | 19717160 A1 | 10/1998 |
| DE | 10026725 A1 | 1/2001 |
| EP | 158823 A2 | 10/1985 |
| EP | 171239 A1 | 2/1986 |
| EP | 1659665 A1 | 5/2006 |
| JP | 2002346374 A | 12/2002 |
| WO | 9709071 A1 | 3/1997 |
| WO | 9730274 A1 | 8/1997 |
| WO | 2004026461 A1 | 4/2004 |

*Primary Examiner* — Kishor Mayekar
(74) *Attorney, Agent, or Firm* — Simpson & Simpson, PLLC

(57) ABSTRACT

The invention relates to a device and method for generating a barrier discharge in a gas flow, comprising a reactor chamber permeable by the gas from an inflow side to an outflow side, a first electrode, a dielectric that shields the reactor chamber against the first electrode, and a second electrode, wherein the second and the first electrode can be switched to connect to a voltage source. To briefly expose a greater portion, preferably all, of the gas flow through the reactor chamber to a plasma, at least two discharge elements associated with the first electrode and made of electrically conductive material protrude at least partially into the reactor chamber and are electrically insulated from each other and the first and second electrodes, and the second electrode is disposed relative to the discharge elements such that discharges occur between the discharge elements and the second electrode in the reactor chamber.

11 Claims, 3 Drawing Sheets

DEVICE AND METHOD FOR GENERATING A BARRIER DISCHARGE IN A GAS FLOW

CROSS-REFERENCE TO RELATED APPLICATION

This application is filed under 35 U.S.C. §120 and §365(c) as a continuation of International Patent Application PCT/EP2011/063358, filed Aug. 3, 2011, which application claims priority from German Patent Application No. 10 2010 044 252.6, filed Sep. 2, 2010, which applications are incorporated herein by reference in their entireties.

FIELD OF THE INVENTION

The present invention relates to a device and method for generating a barrier discharge in a gas flow.

BACKGROUND OF THE INVENTION

Modern oxidizing air cleaning methods apply more often non thermal plasmas for destroying and degrading harmful substances, like smells, allergens and germs, These plasmas generate high reactive radicals, which are able to convert a wide variety of in air carried harmful substances at environmental conditions.

For more than 100 years the plasma treatment of air is known to work according to the principle of the dielectric discharge, known as well as barrier discharge. Large volume, non-thermal plasmas can be generated with dielectric barrier discharge. The dielectric material, preferably gas, is present between electrodes subjected to a high alternating voltage. The dielectric material hinders the movement of the electrons and finally interrupts it. The electrons are not only hindered but also dammed by the dielectric material, whereby an opposing field builds up in opposition to the outer activating field. The opposing field increases until the outer field and the opposing field compensate each other and the flow of electrons comes to a stop. The properties of the dielectric barrier material as well its form determine, beside the arrangement of the inner electrode and the outer electrode, appearance of the discharge, which is characterized by the occurrence of single discharges, the so called is filaments. These filaments appear in a huge number on a short term. They are distributed usually across the whole area of the electrode generating the plasma.

A so called "Siemens-tube" is used as a plasma generator for the oxidative treatment of air. The "Siemens-tube" is made up of a tube like dielectric material which is preferably quartz glass or borosilicate. The inner wall of the tube like dielectric material is lined with an inner electrode. The inner electrode is made of a conductive material is positioned close to the inner glass surface and preferably without an air gap. An outer electrode is arranged on the lateral surface of the dielectric material which is formed by a close fitting mesh, like a steel mesh. In case a high alternating voltage, lie 3-6 kV (kilo Volts) is applied to the inner and outer electrode, a dielectric barriers discharge occurs. In doing so, ions and ozone ($O_3$ and $O_1$) are generated.

During the plasma treatment o a gas flow with the "Siemens-tube" the air flow is guided through the tube like dielectric material. For this purpose the plasma is ignited at the inner electrode. The plasma at the inner electrode forms exclusively in the outer layers of the air flow which come directly in contact with the inner electrode. The much greater portion of the air flow reacts only with ozone and the oxygen ions, which are generated during discharge.

The outer layers of the air flow, which immediately are in contact with the plasma, be more effectively freed from pollutants, in particular of odors and bacteria, because in the plasma the highest energy in the form of free radicals, electrons and ions is present. Furthermore the plasma produces an intense UV radiation in the wavelength range smaller than 300 nm, which can efficiently break molecular bindings of air pollutants.

A problem with the plasma treatment of a gas flow according to the prior art is, that the inner electrode quickly get contaminated by the pollutants contained in the gas stream and thus loses effectiveness. A polluted inner electrode replacement is possible only with great effort and disruption of the plasma treatment.

The German patent application DE 197 17 160 A1 discloses a device for plasma-chemical conversion of exhaust gases, which creates a barrier discharge in the flowing gas. The device includes a reactor room that is flowed through in longitudinal direction from an inlet side to a discharge side of the exhaust gas to be treated. A dielectric that shields the reactor room of the first electrode is attached to the first electrode. A second electrode is placed on the dielectric inside the reactor and formed as a perforated sheet material, where the second electrode against is switchable the first electrode. The two electrodes will be connected for this purpose to an alternating voltage source. When applying the alternating voltage it comes to a gas discharge in the gap area between the structures of the perforated second electrode and the dielectric material. The gas discharge is therefore primarily generated near the surface of the dielectric material. The exhaust gas flowing by is swirled by the perforated sheet like material and briefly enters the excitation region of the plasma. The second limitation of the reactor room is formed by a wall. No discharge is formed between the dielectric material and the wall, closing off the reactor room. As a result, more or less large parts of the gas flow, depending on the distance of the wall, come not directly in contact with the plasma and flow therefore untreated through the reactor room.

The German patent application DE 100 26 725 A1 describes a exhaust gas purification device which has a current passageway formed between a pair of discharge electrodes. A high voltage producing device produces a high voltage between the electrodes to purify exhaust gas emissions. An auxiliary electrode is arranged in the passageway with holes between the discharge electrode and the auxiliary electrode so that electrical discharges can be produced between the electrodes.

The US patent application U.S. 2008/056934 A1 shows that diffusive plasma is for effective treatment of contaminated air and material processing. Air is purified and disinfected by passing through the diffusive plasma device which includes a reactor or a plurality of reactors arranged in parallel or series and is energized by a high voltage alternating current power supply. The diffuser, being electrically isolated, provides extra nucleation sites to initiate discharges The addition of a diffuser, thereby, enhances the overall effectiveness of decomposing chemicals and destroying microbes to achieve high air treatment and material processing performance. The diffuser can be made of suitable filtering materials to additionally serve as a filter. By incorporating suitable catalytic materials with the diffuser, the reactor becomes a catalytic plasma reactor wherein the plasma environment provides enhanced catalytic functions.

The international patent application WO 2004/026461 A1 describes a non-thermal plasma reactor comprising two electrodes and a gas flow path through the reactor. At least one electrode is provided with a multiplicity of triple junctions on or within a surface of the electrode that faces the other electrode. One or both electrodes are covered by pots, stripes or portions of dielectric materials.

The international patent application WO 97/30274 A1 describes a device for the cleaning of exhaust gases from internal combustion engines, in particular a diesel exhaust soot filter. Said device has a discharge electrode, a counter electrode opposite thereto for electrical charging of the exhaust gas components, a ceramic structure with a circular cross-section and ducts extending there through in the direction of flow, and an internal electrode at high voltage.

This electrode is arranged on the inner cylinder wall of the ceramic structure and creates an electrical field at right angles to the ducts passing through said ceramic structure. The soot particles are deposited and oxidized on the walls of the ducts, and a separation is provided to prevent flow through the hollow internal space of the ceramic structure.

Japanese patent application JP 2002-346374 A shows a gas treater with a gas passage through which a gas containing a component to be treated flows. A discharge electrode is disposed in the passage and performing discharge for generating a low-temperature plasma. A functional member and a heater are provided, wherein the heater heats the member. The member is disposed in the passage for treating the component remaining in the gas treated with the discharge of the electrode and is made from a functional material containing a combustion oxidation catalyst.

European patent application EP 1 659 665 A1 describes a discharge device for generating a streamer discharge from the tip of a discharge electrode towards a counter electrode. The discharge electrode in the shape of a wire or rod is disposed substantially parallel to the counter electrode, whereby, even when the tip of the discharge electrode becomes worn out, the shape of the tip of the discharge electrode remains unchanged and the distance between the discharge electrode and the counter electrode remains unchanged.

The international patent application WO 97/09071 A1 provides a method for sterilization of objects. The object that should be sterilized is placed in a closed vessel. The closed is placed between two high voltage electrodes. Applying a high voltage between the said electrodes results in a conversion of oxygen in the air inside the closed vessel into ozone.

U.S. patent application 2003/180199 A1 relates to a plasma reactor for reducing noxious gas by using a plasma reaction, a production method for such a plasma reactor. An emission control apparatus is used for reducing noxious gas contained in exhaust gas of a vehicle by such a plasma reactor.

BRIEF SUMMARY OF THE INVENTION

Starting from the above mentioned prior art it is the object of the present invention to create a device for producing a barrier discharge in a stream of gas, wherein the larger part of the gas flow through the reactor room, preferably the complete gas flow is exposed to the plasma for a short time.

The above object is achieved by a device for generating a barrier discharge in a gas flow. The device comprising:
 a reactor room, in which the gas flow is directed from;
 a first electrode;
 a dielectric material which shields a least the reactor room against the first electrode;
 a second electrode, wherein the first and the second electrode are connected against a voltage source; and
 at least two discharge elements made from an electrical conductive material reach partially into the reactor room and are assigned to the first electrode, wherein the discharge elements are electrically isolated against each other and against the first and second electrode; wherein the discharge elements are embedded in the dielectric material and wherein the second electrode is arranged with respect to the discharge elements, that discharges form between the discharge elements and the second electrode in the reactor room.

A further object of the invention is to develop a process for producing a barrier discharge in a stream of gas, wherein the larger part of the gas flow through the reactor room, preferably the complete gas flow, is exposed to the plasma for a short time.

The above object is achieved by a method for generating a barrier discharge in a gas flow comprising the following steps:
 guiding a the gas flow through a reactor room from a inlet side to a outlet side, wherein the reactor room has a first electrode, a dielectric material which shields the reactor room against the first electrode and a second electrode;
 guiding a the gas flow through a reactor room from a inlet side to a outlet side, wherein the reactor room has a first electrode, a dielectric material which shields the reactor room against the first electrode and a second electrode;
 coupling capacitively at least the first electrode with at least two discharge elements of the first electrode, wherein the discharge elements are at least partially embedded in the dielectric material and reach at least partially into the reactor room;
 generating discharges between the discharge elements and the second electrode, wherein the first and the second electrode are connected against a voltage source and the discharge elements are electrically isolated against each other and against the first and the second electrode; and
 guiding a gas flow in the reactor room through the discharges between the discharge elements and the second electrode.

The discharge elements reaching at least partially into the reactor room are separated electrically from the upstream first electrode by the dielectric material.

The second electrode, also called the counter electrode, is located preferably in or on the inner wall of the reactor room and opposite to the discharge elements stretching into the reactor room.

The capacitive coupling of the discharge elements causes an even distribution of the filaments between the discharge elements and the second electrode connected as counter electrode. The full Galvanic isolation of the discharge elements causes them be lifted to one capacitive level. This has the advantage that the gas discharge at one of the discharge elements does not change the electric potential of the neighboring discharge elements. As a result, a gas discharge of several gas discharge elements can occur at the same time.

The second electrode is arranged with respect to the discharge elements in such a way that discharges arise between the discharge and the second electrode inside the reactor. The simultaneous ignition makes it possible to produce a discharge curtain over the cross-section of the flow path, by which the total gas flow is passed through and directly exposed to the plasma.

An advantage of the arrangement is the local arrangement of filaments. While in a planar dielectric barrier the filaments are ignited from the entire surface (local electrodes are separated by a high transition resistance from the neighboring element), therefore the discharge places can be focused through the discharge elements.

The capacitive coupling of the discharge elements on the first electrode is preferably so, that the discharge elements are arranged on the dielectric material, which shields the reactor room against the first electrode. In order to encourage the gas discharge between the discharge elements and the second electrode, the discharge elements are directed preferably towards the second electrode.

The discharge between the discharge elements and the second electrode can be enhanced further by that at least the protruding portion of the discharge elements into the reactor room is pen-shaped, with the pins in the reactor room preferably phased out in a tip. This results in a concentration or focusing of the charge at the free end of the pins or their tips. At the same time, the power consumption of the device and ozone emissions are reduced.

The trained pen-shaped discharge elements allow an even distribution of gas discharges in the direction of the second electrode. In addition, the distance between the ends or the tip of the pen-shaped discharge elements to the second electrode can be determined by the pin length and thereby the homogeneity of the discharge improves. If the discharge elements are constructed as bending shape parts or as bending stamping parts, respectively, the distance to the second electrode and the homogeneity of the discharge are improved by their shape and arrangement.

If the discharge elements are partially embedded in the dielectric material, which shields the reactor room against the first electrode, the gas discharge elements can be connected during the molding of the dielectric material in a single operation with the dielectric material. In particular, the dielectric material can be produced completely as plastic injection molded part, for example made from PEEK, PA, PTFE, PE or similar materials, wherein the discharge elements and/or the first and second electrode are overmoulded as an insert.

The discharge elements and the electrodes are made from a conductive material, especially copper, stainless steel or other electrically highly conductive materials. The discharge elements can be prefabricated as punched parts or bending shape parts.

As a dielectric material, ceramic, glass, plastic, or a composite are considered, depending on the manufacturing process.

It is constructive advantageous if the second electrode is arranged in the form of a ring electrode on the inner surface of the reactor room. In order to protect of the second electrode against negative influences of the gas flow in the reactor room, particularly against oxidation and dirt, one embodiment of the invention provides that a dielectric material shields the reactor room against the second electrode. This can be the same one piece shaped dielectric material which shields the first electrode against the reactor room. This one piece dielectric material is a moulding part and is a component of the flow channel and at the same time accommodates the plasma producing components.

Particularly effective and targeted the gas flow streaming through the reactor room is exposed to the barrier discharge, in case gas guiding elements are arranged between the inlet side and the discharge side of the reactor room, which divide the gas flow into several partial flows and at least one discharge element is associated with each partial flow. Preferably, the gas guiding elements include multiple flow channels which are arranged in a particular concentric manner with respect to the longitudinal axis of a tubular reactor room. The discharge elements are either immediately adjacent to the discharge side of the flow channels or placed in the flow channels. All the flow channels have preferably a matching length and geometry. The arrangement of the discharge elements in relation to the discharge side of the flow channels or within the flow channels is also preferably identical in all flow channels.

Unless the discharge elements are adjacent to the discharge sides, the second electrode is preferably arranged as a ring-shaped electrode which is concentrically arranged to the discharge sides, immediately behind the discharge sides and in the direction of flow. As far as the discharge elements are arranged within the flow channels, the second electrode is preferably designed as a multi-piece part and one part of the second electrode is arranged in the flow channel Each part of the second electrode must be connected to the power source.

To expose every partial as effectively as possible to the plasma, in the top view to the cross-sectional area of each flow the second electrode and each discharge element are arranged oppositely to each other. It does not matter if the discharge elements and the second electrode are slightly offset to each other in the direction of the flow channel. Especially with a circular cross-sectional area of each of the flow channels an opposite arrangement of the electrode and the discharge elements results in a highly uniform formation of the plasma.

A particularly effective guidance of the gas flow in the reactor room is achieved in that a pipe-shaped reactor room has a moulded part, which is in particular a polymer injection moulded part. The flow channels are arranged in the moulded part for guiding the gas flowing through the reactor room, so that in the region of the flow channels the flow through of the reactor room from the inlet side to the discharge side is divided into a respective number of part flows. Preferably all outlets of the flow channels are located on a concentric circle around the longitudinal axis of the tubular reactor room.

Also concentric with respect to the axis of the tube-shaped reactor room, at least one discharge element is arranged adjacent to each outlet. The discharge elements are preferably on a concentric circle, which has a smaller diameter than the concentric circle, where the outlet ports of the flow channels are arranged.

The second electrode surrounds all outlets of the flow channels in direction of flow behind the vents, so that discharges between the discharge elements and the second electrode form discharge curtains in front of the outlets of the flow channels.

BRIEF DESCRIPTION OF THE DRAWINGS

The nature and mode of operation of the present invention will now be more fully described in the following detailed description of the invention taken with the accompanying drawing figures, in which:

FIG. 3b shows a sectional view along the line A-A of FIG. 3a.

DETAILED DESCRIPTION OF THE INVENTION

Figure 1:
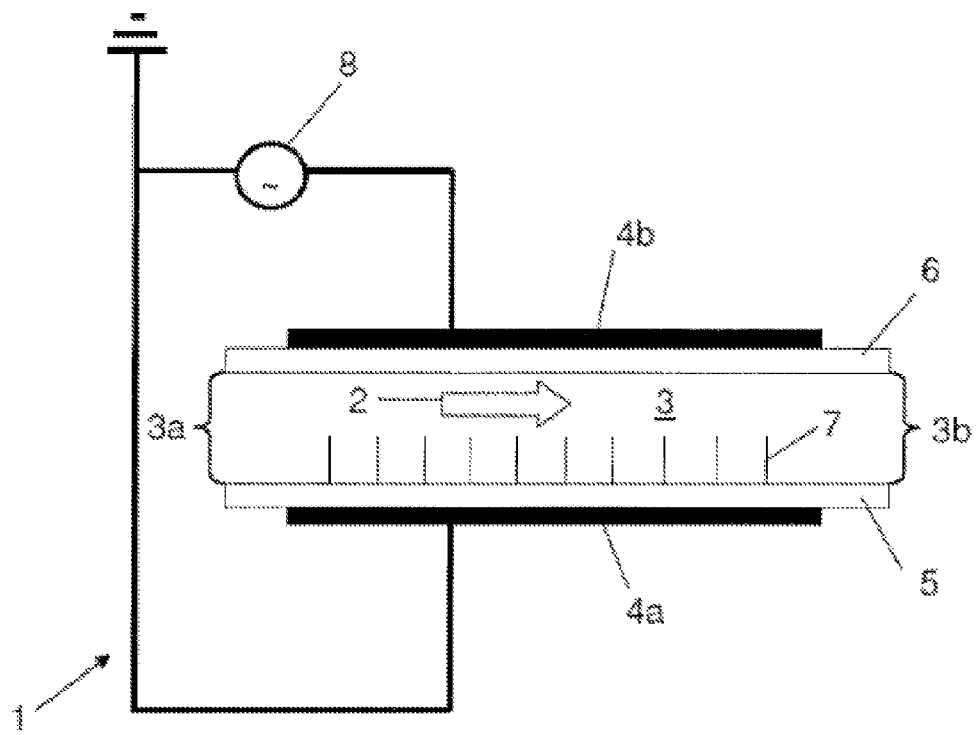
FIG. 1 shows a schematic view of the inventive device for generating a barrier discharge in a stream of gas.

Same reference numerals refer to same elements throughout the various figures. Furthermore, only reference numerals necessary for the description of the respective figure are shown in the figures. The shown embodiments represent only examples of how the invention can be carried out. This should not be regarded as limiting the invention.

FIG. 1 shows a device 1 for the generation of a barrier discharge in a gas flow 2, which id guided through a reactor room 3 from an inlet side 3a to an outlet side 3b.

The reactor room 1 is limited at its base by a two-dimensional first dielectric material 5, which shields the reactor room 1 against the plate-shaped first electrode 4a attached to the base of the reactor room.

The top of the reactor room 3 is limited by a second dielectric material 6, which shields the reactor room against a second disk-shaped electrode 4b. The second dielectric 6 is used to protect of the second electrode 4b against impurities or contaminations. Basically, the device 1 can be formed without the second dielectric material 6.

At the side the reactor room 1 is closed by respective side walls (not shown in the sectional view of FIG. 1). Several rows of ten pen-shaped discharge elements 7 are evenly distributed above the surface of the plate-shaped first electrode 4a. The pen-shaped discharge elements 7 are partially embedded in the dielectric material 5 and extend partially into the reactor room 3. Here are pen-shaped discharge elements 7 are oriented towards the second electrode 4b.

The first and second electrode 4a, 4b are connected against a voltage source 8, which is an alternating voltage or pulsed DC voltage between 1 kV to 20 kV in a frequency range from 50 Hz-500 kHz. The pen-shaped discharge elements 7 are, however, by the dielectric material 5, which is formed in particular of a polymer material, electrically insulated against each other and against the first and second electrode 4a, 4b.

Between the discharge elements 7 oriented on the second electrode 4b and the second electrode 4b discharges occur, through which the gas flow 2 is guided through. The arrangement of the discharge elements 7 is tailored to the flow cross-section of the reactor room 3 and the second electrode 4b, so that the gas flow 2 is completely briefly transformed into the plasma. The dielectric barrier in the form of the dielectric material 5 causes that all pen-shaped discharge elements 7 are lifted to a charge level. A gas discharge at the tip of one of the electrical discharge elements 7 does not change the potential of adjacent pen-shaped discharge elements 7, so that at the same time gas discharges occur at several discharge elements 7.

FIG. 2 shows an embodiment of the inventive device 1 for installation in a piping system, which is flowed through by the gas flow 2. The gas flow 2 flows on the inlet side 3a into the device 1 and flows after the plasma treatment on the outlet side 3b out of the device 1. The device 1 is connectable by flanges with the pipe (not shown) on the inlet side 3a and the outlet side 3b. In particular the device 1 can be replaced quickly and easily for cleaning purposes. The reactor room 3 is a hollow cylindrical tube 9 which is limited at the inlet side 3a and outlet side 3b by a circular flow cross-section.

Between the inlet side 3a and outlet side 3b a moulded part 11 is arranged in the direction of the gas flow 2 in the reactor room 3. Concentric with a longitudinal axis 15 of the device 1 fourteen flow channels 12 are arranged in the moulded part 11, which partition the gas flow 2 over the length of the flow channels 12 of the section of the reactor room 3 into several partial flows 13. In the middle portion of the moulded part 11, surrounded by the flow channels 12, a plate-shaped first electrode 4a is located towards the inlet side 3a of the reactor room 3. The longitudinal axis 15 of the device 1 runs through the centre of the first electrode 4a. The first electrode 4a is embedded in a cylindrical blind hole 16 in the moulded part 11. Immediately adjacent to the outlets 17 of each flow channel 12 a pen-shaped discharge element 7 is arranged in the moulded part 11. A section of each pen-shaped discharge element 7 is embedded in the moulded part 11, which I made of dielectric material, while a remaining section 7a of the pen-shaped discharge element 7 protrudes in the reactor room 3. The remaining section 7a protruding into the reactor room 3 is visible in FIG. 1. The pen-shaped discharge elements 7 are embedded parallel and concentric to the longitudinal axis 15 approved for in the moulded part 11. The second electrode 4b is designed as a ring electrode and rests against the inner surface of the cylindrical tube 9 on the outlet side 3b.

In the top view, which is in the direction onto the outlets 17 of the flow cross-section of each flow channel 12, the second electrode 4b and the respective associated discharge elements 7, 7a are arranged on opposite sides of the flow channel 12, wherein between each of the in the reactor room 3 protruding section 7a of the discharge element 7 and the ring-shaped second electrode 4 a slight offset exists in the direction of the longitudinal axial 15, which is however harmless to the formation of discharges 18 between each discharge element 7, 7a and the second electrode 4b.

The bottom area of the blind hole 16 is made of dielectric material, which shields the reactor room 3 against the first electrode 4a provided in the blind hole 16. Preferably also the dead space in the blind hole 16, located opposite to the flow direction, is filled with dielectric material.

Figure 2A:
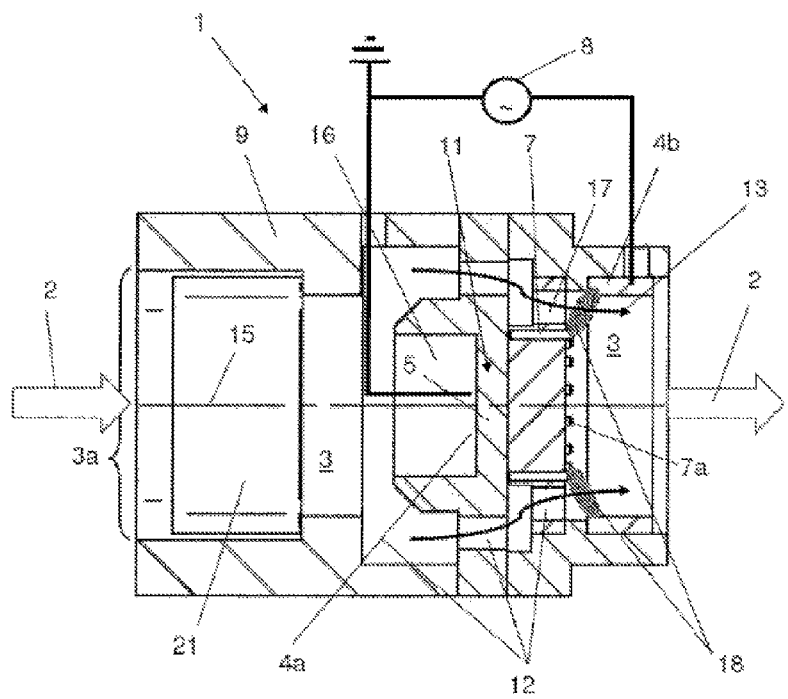
FIG. 2a shows a sectioned view of the invention device for installation in a gas pipe.
Figure 2B:
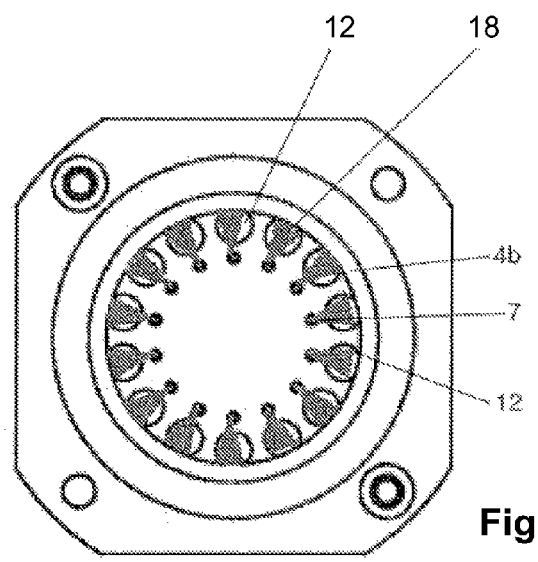
FIG. 2b shows the device according to FIG. 2a in side view.

From the side view of FIG. 2b it is recognizable, that in front of each outlet the discharges 18 have the form similar to a discharge curtain, which is formed between the discharge elements 7, 7a and the outlets 17 surrounding second electrode 4b. As a result, the partial flows 13 of the gas flow 2 are guided through the as gas guiding means acting flow channels 12 and are passed through the plasma. Accordingly, the entire gas flow 2 is subjected directly to the plasma.

Figure 3A:
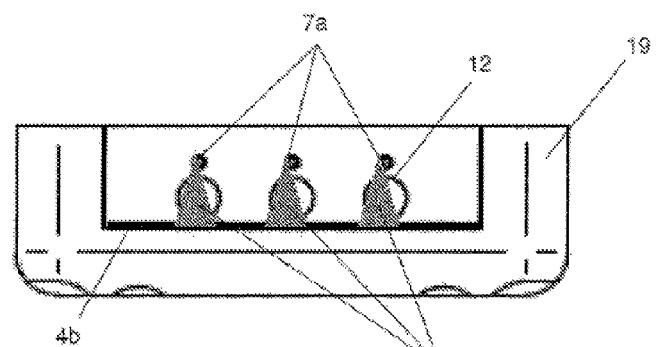
FIG. 3a shows a side view of another embodiment of the invention as a substructure option.
Figure 3B:
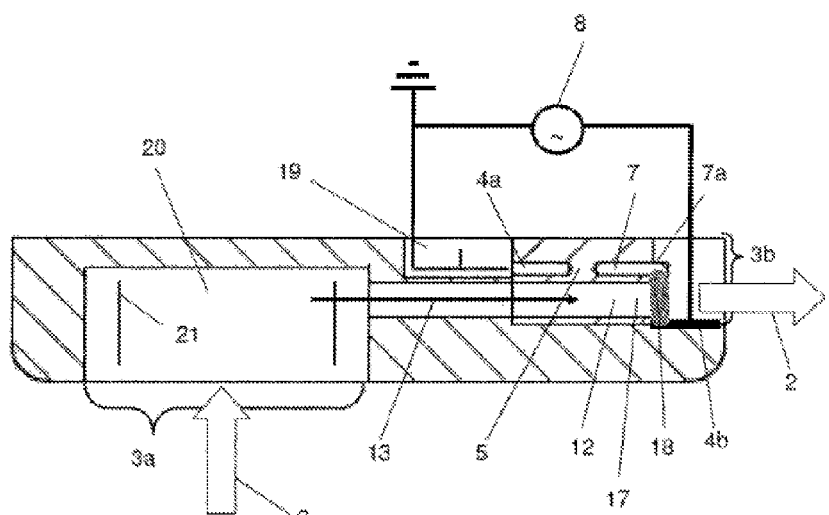

FIGS. 3a, 3b show another embodiment of the inventive device 1, which is designed as a built-in unit. The housing of the reactor room 3 is mounted from under a plate, for example a table, by screws or clips. A sufficiently dimensioned space 20 is located at the inlet side 3a of the reactor room 3 which hosts an electrically operated fan 21 (only indicated), whose fan wheel rotates around a not shown axis, which is vertical in the representation shown here. The fan 21 forces the gas flow of air through the reactor room 3 from the inlet side 3a to the outlet side 3b.

From the side wall of the space 20 a total of three flow channels 12 stretch in the direction of the outlet side 3b of the reactor room 3, which divide the gas flow 2 as shown in the embodiment according to FIGS. 2a, 2b into several partial flows 13. Above the outlets 17 three pen-shaped discharge elements 7are arranged in the housing 19 of the device 1, wherein remaining sections 7a are placed immediately adjacent above the outlets 17 outputs and reach into the reactor room 3.

The dielectric material 5, which has the form of the housing 19, shields the embedded first electrode 4a against the reactor room 3. Below the outlets 17, in the direction of flow, the second electrode 4b, located behind the outlets 17 and has the form of a plate-shaped electrode.

As shown in FIG. 3a the plate-shaped second electrode 4b extends across the entire width of the reactor room 3 at the outlet side 3b. Furthermore, it is apparent from FIG. 3a, that in a top view on the flow cross-section of flow channels 12 it is clear that the second electrode 4b and the three discharge elements 7, 7a are arranged on opposite sides of the flow channels 12. With this arrangement of the second electrode 4b with respect to the discharge elements 7, 7a it is ensured that the discharges 18 form between the discharge elements 7, 7a and the second electrode 4b and the overall gas flow 2, divided into partial flows 13 is passed through the plasma.

The cleaned gas flow 2 leaves the device 1 at the outlet side 3b.

The invention has been described with reference to specific embodiments. It is obvious to a person skilled in the art, however, that alterations and modifications can be made without leaving the scope of the subsequent claims.

LIST OF REFERENCE NUMBERS 1 device
2 gas flow
3 reactor room
3*a* inlet side
3*b* outlet side
4*a* first plate-shaped electrode
4*b* second disk-shaped electrode
5 first dielectric material
6 second dielectric material
7 pen-shaped discharge elements
7*a* remaining section
9 hollow cylindrical tube
11 moulded part
12 flow channel
13 partial flows
15 longitudinal axis
16 blind hole
17 outlets
18 discharges
19 housing
20 space
21 fan

What is claimed is:

1. Device for generating a barrier discharge in a gas flow comprising:
    a reactor room, in which the gas flow is directed from;
    a first electrode;
    a dielectric material which shields a least the reactor room against the first electrode;
    a second electrode, wherein the first and the second electrode are connected against a voltage source; and
    at least two discharge elements made from an electrical conductive material reach partially into the reactor room and are assigned to the first electrode, wherein the discharge elements are electrically isolated against each other and against the first and second electrode; wherein the discharge elements are embedded in the dielectric material and wherein the second electrode is arranged with respect to the discharge elements, that discharges form between the discharge elements and the second electrode in the reactor room.

2. Device according to claim 1, wherein the discharge elements are oriented in a direction towards the second electrode.

3. Device according to claim 1, wherein at least a section of the discharge elements which stretch into the reactor room are pin formed.

4. Device according to claim 1, wherein the discharge elements end in the reactor room with a tip or an edge.

5. Device according to claim 1, wherein the dielectric material, which shields the reactor room against the first and/or the second electrode, is an injection moulded part.

6. Device according to claim 1, wherein the first electrode is attached to the dielectric material or is arranged in neighboring position to it.

7. Device according to claim 1, wherein the second electrode is positioned at an inner surface of the reactor room.

8. Device according to claim 1, wherein the dielectric material shields the reactor room against the second electrode.

9. Device according to claim 1, wherein the gas flow is divided between the inlet side to the outlet side into several partial gas flows and each partial gas flow has at least one discharge element.

10. Device according to claim 9, wherein the partial gas flow is made from several flow channels, which are arranged concentrically with respect to a longitudinal axis of the reactor room and wherein the reactor is of
    a tube.

11. Device according to claim 10, wherein the second electrode and each discharge element are arranged on opposing sides of the flow channel.

* * * * *